US010195099B2

(12) United States Patent
Hepler et al.

(10) Patent No.: US 10,195,099 B2
(45) Date of Patent: Feb. 5, 2019

(54) METHOD AND SYSTEM FOR INTERMITTENTLY ASSISTING BODY MOTION

(71) Applicant: Bionic Power Inc., Vancouver (CA)

(72) Inventors: Daniel Loren Hepler, Vancouver (CA); Clive Edward Mullins, North Vancouver (CA)

(73) Assignee: Bionic Power Inc., Vancouver (CA)

( * ) Notice: Subject to any disclaimer, the term of this patent is extended or adjusted under 35 U.S.C. 154(b) by 541 days.

(21) Appl. No.: 14/992,941

(22) Filed: Jan. 11, 2016

(65) Prior Publication Data
US 2017/0196750 A1 Jul. 13, 2017

(51) Int. Cl.
*A61H 3/00* (2006.01)
*A61F 2/72* (2006.01)
(Continued)

(52) U.S. Cl.
CPC ........... *A61H 3/00* (2013.01); *A61B 5/04888* (2013.01); *A61B 5/112* (2013.01); *A61F 2/72* (2013.01);
(Continued)

(58) Field of Classification Search
CPC .... A61H 3/00; A61H 1/024; A61H 2201/164; A61H 2201/5061; A61H 2201/5069;
(Continued)

(56) References Cited

U.S. PATENT DOCUMENTS 1,184,056 A 5/1916 Van Deventer
1,472,335 A 5/1922 Luzy
(Continued)

FOREIGN PATENT DOCUMENTS

CA 2630198 2/2007
WO 99/05991 2/1999
(Continued)

OTHER PUBLICATIONS

Patent Cooperation Treaty International Search Report with a dated Mar. 6, 2017 issued for the parent application assigned International Application No. PCT/CA2017/050012 with an International Filing Date of Jan. 6, 2017.
(Continued)

*Primary Examiner* — Quang D Thanh
(74) *Attorney, Agent, or Firm* — Damien G. Loveland (57) ABSTRACT

Motion of a body segment is assisted when the body segment is moving in a positive power mode but not when it is moving in a negative power mode. When the motion of the body segment is cyclical, for example during walking, assistance to the body segment is switched on and off throughout the cycle to correspond to positive and negative power modes respectively. Energy used to assist the body segment may be harvested from prior motion of the body segment, either in prior cycles and/or when the body segment is moving in a negative power mode. The energy used may also be harvested from other body segments. Assisting motion of a body segment may be used to reduce the metabolic cost of locomotion, or to reduce exertion, when walking, jogging, running or sprinting.

18 Claims, 5 Drawing Sheets

(51) Int. Cl.
*A61H 1/02* (2006.01)
*A61B 5/11* (2006.01)
*A61N 1/36* (2006.01)
*F03G 7/08* (2006.01)
*A61B 5/0488* (2006.01)
*F03G 5/06* (2006.01)
*H02J 7/14* (2006.01)

(52) U.S. Cl.
CPC ......... *A61H 1/024* (2013.01); *A61N 1/36003* (2013.01); *F03G 5/06* (2013.01); *F03G 7/08* (2013.01); *H02J 7/14* (2013.01); *A61H 2201/1207* (2013.01); *A61H 2201/164* (2013.01); *A61H 2201/5007* (2013.01); *A61H 2201/5061* (2013.01); *A61H 2201/5064* (2013.01); *A61H 2201/5069* (2013.01); *A61H 2201/5079* (2013.01); *A61H 2201/5084* (2013.01); *A61H 2230/605* (2013.01)

(58) Field of Classification Search
CPC .... A61H 2201/5064; A61H 2201/5084; A61H 2230/605; A61H 2201/5007; A61H 2201/1207; H02J 7/14; F03G 5/06; F03G 7/08; A61N 1/36003; A61B 5/04888; A61B 5/112; A61F 2/72
See application file for complete search history.

(56) References Cited

U.S. PATENT DOCUMENTS

| | | | |
|---|---|---|---|
| 3,358,678 A | 12/1967 | Kultsar | |
| 3,573,479 A | 4/1971 | Reith | |
| 3,631,542 A | 1/1972 | Potter | |
| 3,820,168 A | 6/1974 | Horvath | |
| 4,065,815 A | 1/1978 | Sen-Jung | |
| 4,569,352 A | 2/1986 | Petrofsky et al. | |
| 4,697,808 A | 10/1987 | Larson et al. | |
| 4,711,242 A | 12/1987 | Petrofsky | |
| 4,760,850 A | 8/1988 | Phillips et al. | |
| 4,781,180 A | 11/1988 | Solomonow | |
| 4,895,574 A | 1/1990 | Rosenberg | |
| 4,953,543 A | 9/1990 | Grim et al. | |
| 5,062,857 A | 11/1991 | Berringer et al. | |
| 5,090,138 A | 2/1992 | Borden | |
| 5,112,296 A | 5/1992 | Beard et al. | |
| 5,133,773 A | 7/1992 | Sawamura et al. | |
| 5,133,774 A | 7/1992 | Sawamura et al. | |
| 5,201,772 A | 4/1993 | Maxwell | |
| 5,282,460 A | 2/1994 | Boldt | |
| 5,344,446 A | 9/1994 | Sawamura et al. | |
| 5,358,461 A | 10/1994 | Bailey et al. | |
| 5,443,524 A | 8/1995 | Sawamura et al. | |
| 5,476,441 A | 12/1995 | Durfee et al. | |
| 5,571,205 A | 11/1996 | James | |
| 5,616,104 A | 4/1997 | Mulenberg et al. | |
| 5,628,722 A | 5/1997 | Solomonow et al. | |
| 5,888,212 A | 3/1999 | Petrofsky et al. | |
| 5,888,213 A | 3/1999 | Sears et al. | |
| 5,893,891 A | 4/1999 | Zahedi | |
| 5,917,310 A | 6/1999 | Baylis | |
| 5,980,435 A | 11/1999 | Joutras et al. | |
| 5,982,577 A | 11/1999 | Brown | |
| 5,992,553 A | 11/1999 | Morrison | |
| 6,113,642 A | 9/2000 | Petrofsky et al. | |
| 6,133,642 A | 10/2000 | Hutchinson | |
| 6,281,594 B1 | 8/2001 | Sarich | |
| 6,291,900 B1 | 9/2001 | Tiemann et al. | |
| 6,293,771 B1 | 9/2001 | Haney et al. | |
| 6,379,393 B1 | 4/2002 | Mavroidis et al. | |
| 6,423,098 B1 | 7/2002 | Biedermann | |
| 6,500,138 B1 | 12/2002 | Irby et al. | |
| 6,517,503 B1 | 2/2003 | Nall et al. | |
| 6,517,585 B1 | 2/2003 | Zahedi et al. | |
| 6,610,101 B2 | 8/2003 | Herr et al. | |
| 6,645,252 B2 | 11/2003 | Asai et al. | |
| 6,673,117 B1 | 1/2004 | Sass et al. | |
| 6,719,806 B1 | 4/2004 | Zahedi et al. | |
| 6,755,870 B1 | 6/2004 | Biedermann et al. | |
| 6,764,520 B2 | 7/2004 | Deffenbaugh et al. | |
| 6,768,246 B2 | 7/2004 | Pelrine et al. | |
| 6,770,045 B2 | 8/2004 | Nall et al. | |
| 6,852,131 B1 | 2/2005 | Chen et al. | |
| 6,910,992 B2 | 6/2005 | Arguilez | |
| 6,911,050 B2 | 6/2005 | Molino et al. | |
| 6,955,692 B2 | 10/2005 | Grundei | |
| 6,966,882 B2 | 11/2005 | Horst | |
| 7,029,500 B2 | 4/2006 | Martin | |
| 7,045,910 B2 | 5/2006 | Kitamura et al. | |
| 7,056,297 B2 | 6/2006 | Dohno et al. | |
| 7,137,998 B2 | 11/2006 | Bedard | |
| 7,147,667 B2 | 12/2006 | Bedard | |
| RE39,961 E | 12/2007 | Petrofsky et al. | |
| 7,304,398 B1 | 12/2007 | Kim et al. | |
| 7,314,490 B2 | 1/2008 | Bedard et al. | |
| 7,367,958 B2 | 5/2008 | McBean et al. | |
| 7,396,337 B2 | 7/2008 | McBean et al. | |
| 7,402,915 B2 | 7/2008 | Hutchinson et al. | |
| 7,410,471 B1 | 8/2008 | Campbell et al. | |
| 7,429,253 B2 | 9/2008 | Shimada et al. | |
| 7,431,737 B2 | 10/2008 | Ragnarsdottir et al. | |
| 7,445,606 B2 | 11/2008 | Rastegar et al. | |
| 7,485,152 B2 | 2/2009 | Haynes et al. | |
| 7,659,636 B2 | 2/2010 | Donelan et al. | |
| 8,579,771 B2 | 11/2013 | Rastegar et al. | |
| 2001/0029343 A1 | 10/2001 | Seto et al. | |
| 2001/0029400 A1 | 10/2001 | Deffenbaugh et al. | |
| 2002/0052663 A1 | 5/2002 | Herr et al. | |
| 2003/0170599 A1 | 9/2003 | Hart | |
| 2004/0039454 A1 | 2/2004 | Herr et al. | |
| 2004/0049290 A1 | 3/2004 | Bedard | |
| 2004/0059433 A1 | 3/2004 | Slemker et al. | |
| 2004/0064195 A1 | 4/2004 | Herr | |
| 2004/0072657 A1 | 4/2004 | Arguilez | |
| 2004/0088057 A1 | 5/2004 | Bedard | |
| 2004/0111163 A1 | 6/2004 | Bedard et al. | |
| 2004/0181289 A1 | 9/2004 | Bedard et al. | |
| 2004/0183306 A1 | 9/2004 | Rome | |
| 2004/0186591 A1 | 9/2004 | Lang | |
| 2005/0184878 A1 | 8/2005 | Grold et al. | |
| 2006/0046907 A1 | 3/2006 | Rastegar et al. | |
| 2006/0046908 A1 | 3/2006 | Rastegar et al. | |
| 2006/0046910 A1 | 3/2006 | Rastegar et al. | |
| 2006/0069448 A1 | 3/2006 | Yasui | |
| 2006/0122710 A1 | 6/2006 | Bedard | |
| 2006/0155385 A1 | 7/2006 | Martin | |
| 2006/0211956 A1* | 9/2006 | Sankai | A61B 5/04888 601/5 |
| 2006/0249315 A1 | 11/2006 | Herr et al. | |
| 2006/0260620 A1 | 11/2006 | Kazerooni et al. | |
| 2007/0016329 A1 | 1/2007 | Herr et al. | |
| 2007/0043449 A1 | 2/2007 | Herr et al. | |
| 2007/0050044 A1 | 3/2007 | Haynes et al. | |
| 2007/0056592 A1 | 3/2007 | Angold et al. | |
| 2007/0233279 A1 | 10/2007 | Kazerooni et al. | |
| 2008/0288088 A1 | 11/2008 | Langenfeld et al. | |
| 2009/0192619 A1 | 7/2009 | Martin et al. | |
| 2010/0130894 A1* | 5/2010 | Ikeuchi | A61H 3/008 601/34 |
| 2011/0166489 A1 | 7/2011 | Angold et al. | |
| 2012/0259431 A1 | 10/2012 | Han et al. | |
| 2013/0056981 A1 | 3/2013 | Mullins et al. | |
| 2014/0276262 A1 | 9/2014 | Kare et al. | |
| 2015/0127018 A1* | 5/2015 | Lim | A61H 3/00 606/130 |
| 2015/0134079 A1 | 5/2015 | Yoon et al. | |

(56) References Cited

U.S. PATENT DOCUMENTS

| | | | |
|---|---|---|---|
| 2015/0164660 A1 | 6/2015 | Will et al. | |
| 2015/0209214 A1* | 7/2015 | Herr | A61H 3/00 623/27 |

FOREIGN PATENT DOCUMENTS

| | | |
|---|---|---|
| WO | 01/65615 | 9/2001 |
| WO | 2004019832 | 3/2004 |
| WO | 2006078871 | 7/2006 |
| WO | 2006113520 | 10/2006 |
| WO | 2007025116 | 3/2007 |
| WO | 2007103579 | 9/2007 |

OTHER PUBLICATIONS

Patent Cooperation Treaty Written Opinion of the International Searching Authority with a dated Mar. 6, 2017 issued for the parent application assigned International Application No. PCT/CA2017/050012 with an International Filing Date of Jan. 6, 2017.

Antaki, J.F., et al., A gait-powered autologous battery charging system for artificial organs, Asaio J, 1995.41(3): p. M588-95.

Brooks, GA, T.D. Fahey, and T.P. White, Exercise physiology: human bioenergetics and its applications. 2nd ed. 1996, Mountain View, Calif.: Mayfield Pub. iii, 750.

Bussolari, S.R. and E.R. Nadel, The physiological limits of long-duration human power production-lessons learned from the Deadalus project. Human Power, 1989. 7(4): p. 1-16.

Donelan, J.M., R. Kram, and A.O. Kuo, Mechanical and metabolic determinants of the preferred step width in human walking. Proceedings of the Royal Society of London Series B-Biological Sciences, 2001. 268(1480): p. 1985-1992.

Donelan, J.M., R. Kram, and A.O. Kuo, Mechanical work for step-to-step transitions is a major determinant of the metabolic cost of human walking. Journal of Experimental Biology, 2002. 205(Pt 23): p. 3717-27.

Donelan, J.M., R. Kram, and A.O. Kuo, Simultaneous positive and negative external mechanical work in human walking. Journal of Biomechanics, 2002. 35(1): p. 117-124.

Drake, J., The greatest shoe on earth, in Wired. 2001. p. 90-100.

Enoka, R.M., Load-Related and Skill-Related Changes in Segmental Contributions to a Weightlifting Movement. Medicine and Science in Sports and Exercise. 1988. 20(2): p. 178-187.

Gonzalez, J.L., A. Rubio, and F. Moll. A prospect on the use of piezolelectric effect to supply power to wearable electronic devices. In ICMR. 2001. Akita, Japan.

Hamilton, B., FAQ: Automotive Gasoline. Retrieved May 12, 2005, from http:/fwww.uvi.edu/Physics/SCI3xxWeb/Energy/GasolineFAQ.html.

Hof, A.L., et al., Speed dependence of averaged EMG profiles in walking. Gait & Posture, 2002. 16(1): p. 78-86.

Koerner, B.I., Rise of the Green Machine, in Wired. 2005.

Kokubo, T., et al., Bioactive metals: preparation and properties. J Mater Sci Mater Med, 2004. 15(2): p. 99-107.

Kymissis, J., et al. Parasitic Power Harvesting in Shoes. in Second IEEE International Conference on Wearable Computing. 1998: IEEE Computer Society Press.

Margaria, R. , Biomechanics and energetics of muscular exercise. 1976, Oxford [Eng.]: Clarendon Press. x, 146 p.

Moll, F. and A. Rubio. An approach to the analysis of wearable body-powered systems. In MIXDES. 2000. Gdynia, Poland.

Nadel, E.R. and S.R. Bussolari, The Daedalus Project—Physiological Problems and Solutions. American Scientist, 1988. 76(4): p. 351-360.

Niu, P., et al. Evaluation of Motions and Actuation Methods for Biomechanical Energy Harvesting. in 35th Annual IEEE Power Electronics Specialists Conference. 2004. Aachen, Germany: IEEE.

Paradiso. J.A. and T. Starner, Energy scavenging for mobile and wireless electronics, IEEE Pervasive Computing, 2005. 4(1): p. 18-27.

Pugh, LG., The influence of wind resistance in running and walking and the mechanical efficiency of work against horizontal or vertical forces. J Physiol, 1971. 213(2): p. 255-76.

Rome, LC. et al., Generating Electricity while Walking with Loads. Science, vol. 309, p. 1725-1728, Sep. 9, 2005.

Saez, L.M., Energy Harvesting from Passive Human Power. PhD Thesis, Jan. 2004, from http://pmos.upc.es/blues/projects/thesis_project_mateu.pdf.

Shenck, N.S. and 1.A. Paradiso, Energy scavenging with shoe-mounted piezoelectrics. IEEE Micro, 200 I. 21 (3): p. 30-42.

Soule, R.G. and RF. Goldman, Energy Cost of Loads Carried on Head, Hands, or Feel. Journal of Applied Physiology, 1969.27(5): p. 687-&.

Starner, T. and J.A. Paradiso, Human generated power for mobile electronics, in Low-power electronics design, C. Piguet, Editor. 2004, CRC Press: Boca Raton.

Starner, T., Human-powered wearable computing. IBM Systems Journal, 1996. 35(3-4): p. 618-629.

ThermoAnalytics, I., Battery type and characteristics. Retrieved 10 Jun. 2, 2005, from http://fwww.thermoanalytics.com/support/publications/batterytypesdoc.html.

Thompson, C., Battery not included. Why your laptop is always running out of juice, in Slate. 2004.

Vogel, S. , Prime mover: a natural history of muscle. 1st ed. 2001 , New York: Norton. xi, 370 p.

Webb, P., et al., The Work of Walking—a Calorimetric Study. Medicine and Science in Sports and Exercise. 1988. 20(4): p. 331-337.

Whitt, F.R.. and D.G. Wilson, Bicycling science. 2nd ed. 1982, Cambridge, Mass.: MIT Press. xviii, 364.

Winter, D.A. and D.A. Winter, Biomechanics and motor control of human movement. 2nd ed. 1990, New York: Wiley. xvi, 277.

Woledge, R.C., N.A. Curtin, and E. Homsher, Energetic aspects of muscle contraction. 1985, London; Orlando: Academic Press. xiii, 359.

* cited by examiner

METHOD AND SYSTEM FOR INTERMITTENTLY ASSISTING BODY MOTION

TECHNICAL FIELD

This application relates to a method and system for assisting motion of one or more body segments. More specifically, this application relates to the intermittent assistance of body segment motion, during periods when the motion of the body segment is in a positive power mode, for example when it is extending and pushing off of something.

BACKGROUND

Energy may be harvested from the movement of body joints of humans and other animals by converting mechanical energy derived from such movement to electrical energy. Activities where body joints move repeatedly, such as walking, jogging, and running, for example, present opportunities to harvest energy from moving body joints over an extended period of time. In some energy harvesting devices and methods, a generator driven by joint motion is coupled to an electrical load. Since the instantaneous mechanical power provided by body joints during repetitive or cyclical activities typically varies over the period of each cycle, both the harvested electrical power supplied to the load and the associated forces applied to the body joint may be time-varying over each cycle.

Muscles may be described as working in a positive mechanical power mode or a negative mechanical power mode. A positive mechanical power mode exists when the product of angular velocity and torque about the associated body joint is positive, i.e. the knee joint is extending and pushing against the external force of gravity on the body away from the ground, or flexing and pulling the foot off the ground against the external force of gravity. A negative mechanical power mode exists when the product of angular velocity and torque about the associated body joint is negative, i.e. the knee joint is extending but resisting that extension, or flexing but resisting that flexion. Generator torque developed by a harvesting generator always counteracts or opposes motion of a body segment. The generator torque acts against muscles operating on a body segment that is moving in a positive mechanical power mode, thereby increasing the work that must be done by the muscles to move body segment. Harvesting energy from the movement of a body segment when associated muscles are operating in a positive mechanical power mode may be referred to as "non-mutualistic" energy harvesting, since the generator torque associated with such energy harvesting acts against muscles and generally increases the metabolic cost of the associated body segment motion. In contrast, generator torque aids muscles operating on a body segment that is moving in a negative mechanical power mode. Harvesting energy from the movement of a body segment when muscles associated with a body segment are operating in a negative mechanical power mode may be referred to as "mutualistic" energy harvesting, since it aids muscles and generally reduces the metabolic cost of the associated body segment motion.

Some energy harvesters are configured to preferentially harvest energy mutualistically by synchronizing energy harvesting to negative power modes of body segment. In some such harvesters, control logic achieves such synchronization based on one or more sensed characteristics of the motion of the host to which the body segment belongs. For example, control logic may synchronize energy harvesting to particular gait phase ranges, which it determines based on one or more sensed characteristics of the motion of the host to which body segment belongs.

Figure 1:
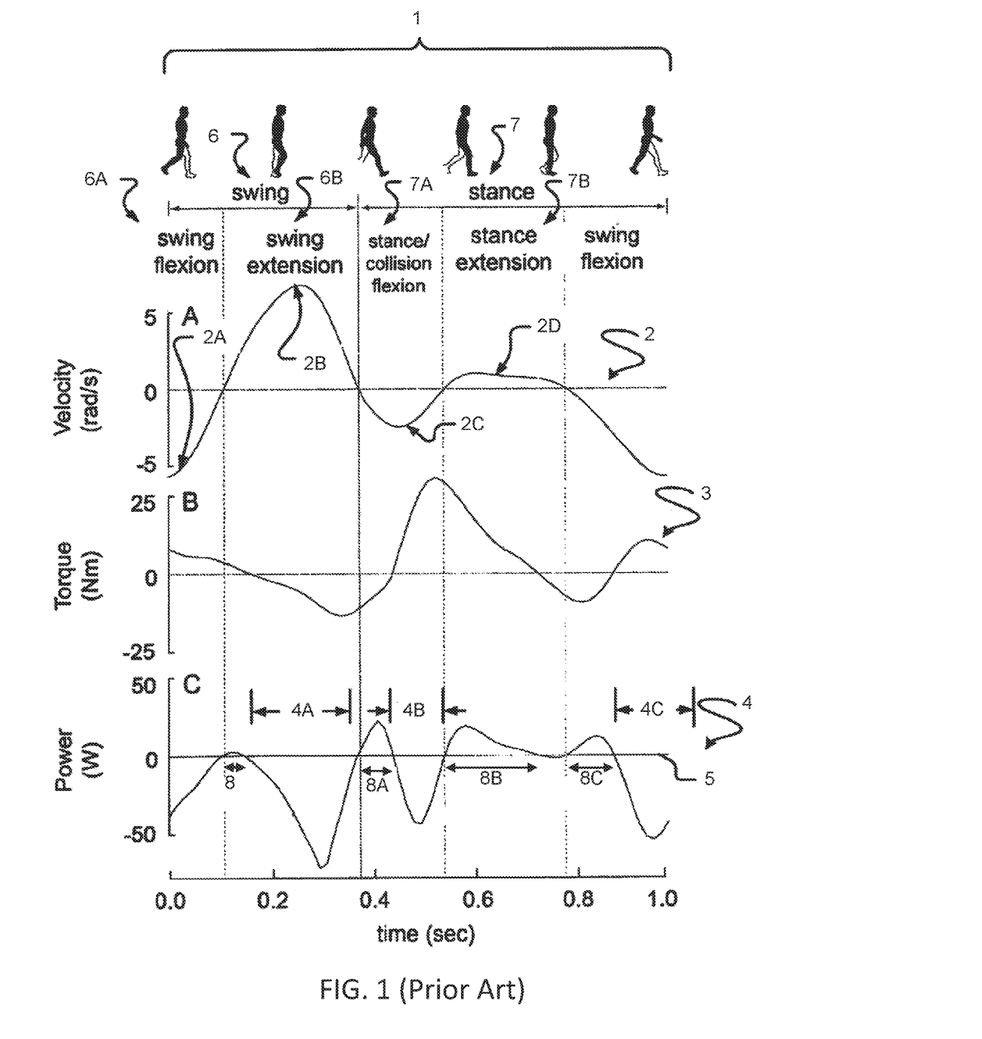
FIG. 1 shows prior art plots of angular velocity, torque and mechanical power, which relate to typical dynamics of a knee joint during a walking gait cycle.

FIG. 1 includes plots that are representative of various quantities relating to typical dynamics of a knee joint during a walking gait cycle 1. In graph A, plot 2 represents the angular velocity of the knee joint (i.e. the time derivative of the angle of the knee joint), where positive angular velocity represents movement in the knee extension direction and negative angular velocity represents movement in the knee flexion direction. In graph B, plot 3 represents the moment of the knee joint, where a positive moment represents torque in the extension direction and a negative moment represents torque in the flexion direction. In graph C, plot 4 represents the mechanical power associated with movement of the knee joint, where positive mechanical power represents power that increases the mechanical energy of the knee. Mechanical power (plot 4) represents the product of the torque (plot 3) and the angular velocity (plot 2) of the knee joint. The integral of the mechanical power (plot 4) represents the mechanical work performed by the knee joint. Beyond the knee joint, the total mechanical work expended during walking includes work performed by other parts of the body, such as the ankles, the toes, the hips and the arms.

Referring to FIG. 1, gait cycle 1 may generally be divided into a swing portion 6 and a stance portion 7. During the swing portion 6, the foot corresponding to the shaded knee (i.e. the right knee) is off of the ground. In the stance portion 7, the foot corresponding to the shaded knee is on the ground. Swing portion 6 may be further divided into a swing flexion portion 6A, during which the knee is flexing, and a swing extension portion 6B, during which the knee is extending. Stance portion 7 may be further divided into a stance/collision flexion portion 7A, during which the knee is flexing, and a stance extension portion 7B, during which the knee is extending. During one gait cycle 1, angular velocity plot 2 comprises extrema 2A, 2B, 2C and 2D which occur, respectively, in swing flexion portion 6A, swing extension portion 6B, stance/collision flexion portion 7A and stance extension portion 7B. These extrema correspond to the end of acceleration of the knee joint.

In plot 4, muscles are acting to decrease the mechanical energy of the knee joint in negative power intervals 4A, 4B and 4C of power plot 4. In interval 4A, knee flexor muscles are acting against the extension that occurs during swing extension in order to arrest extension of the knee prior to heel strike. In interval 4B, knee extensor muscles are acting against the flexion that occurs during stance/collision flexion when the mass of the human is transferred to the foot shortly after heel strike. In interval 4C, knee extensor muscles are acting against the flexion that occurs during swing flexion in order to arrest flexion of the knee prior to the start of swing extension. The knee is working in a positive power mode in interval 8, as it is in intervals 8A, 8B and 8C.

This background information is provided to reveal information believed by the applicant to be of possible relevance to the present invention. No admission is necessarily intended, nor should be construed, that any of the preceding information constitutes prior art against the present invention.

SUMMARY OF INVENTION

The present invention is directed to a method and system for intermittently assisting motion of a body segment, during periods when the body segment is moving in a positive power mode. When the motion of the body segment is cyclical, for example during walking, the power mode may alternate between positive and negative modes, with the system providing energy to the body segment during only the positive power modes. Energy used to assist the body segment may have been previously harvested from motion of the body segment, either in a mutualistic mode, a non-mutualistic mode, or both. Within a cycle of body motion, energy may alternately be harvested from and supplied back to a body segment.

The body-segment motion assisting system of the present invention may be used, for example, to provide help to the host or wearer of such a system during cyclical motions, particularly of the knee joint. It may be used to reduce the metabolic cost of locomotion, or to reduce exertion, when walking, jogging, running or sprinting.

Disclosed herein is a system for intermittently assisting movement of a body segment comprising: a motor-generator; a mechanical linkage configured to transmit mechanical power from the motor-generator to the body segment; and a circuit configured to supply current to the motor-generator when the body segment is moving in a positive power mode, said circuit configured to prevent supply of current to the motor-generator when the body segment is moving in a negative power mode.

In some embodiments, the movement of the body segment is repeated over a plurality of cycles and the circuit is configured to supply current to the motor-generator multiple times within each cycle. In some embodiments, the circuit is configured to draw current from the motor-generator when the body segment is moving in a negative power mode. In some embodiments, the movement of the body segment is repeated over a plurality of cycles and the circuit is configured to supply current to and draw current from the motor-generator multiple times within each cycle. In some embodiments, the circuit continually controls an amount of the current which is supplied to the motor-generator when the body segment is moving in the positive power mode. Some embodiments include one or more sensors configured to detect one or more parameters of movement or muscle activity of the body segment, and the circuit is configured to receive signals from said sensors and supply current to or draw current from the motor-generator based on said signals. In some embodiments, the circuit comprises logic for estimating when the body segment is moving in a positive power mode and when the body segment is moving in a negative power mode. In some embodiments, the circuit comprises a bridge that functions both as a rectifier when current is drawn from the motor-generator and as an inverter when current is supplied to the motor-generator.

Further disclosed herein is a method for intermittently assisting movement of a body segment comprising: mechanically linking a motor-generator to the body segment such that mechanical power produced by the motor-generator assists movement of the body segment; identifying positive power modes of said movement; supplying current to the motor-generator when the body segment is moving in a positive power mode; and preventing supply of current to the motor-generator when the body segment is moving in other than a positive power mode.

In some embodiments, wherein the movement of the body segment is repeated over a plurality of cycles, the method may further comprise: supplying the current to the motor-generator multiple times within each cycle; and drawing current from the motor-generator when the body segment is moving in a negative power mode. In some embodiments, the method further comprises continually controlling an amount of the current which is supplied to the motor-generator when the body segment is moving in the positive power mode. In some embodiments, the method further comprises: sensing one or more parameters of movement or muscle activity of the body segment; receiving signals from said sensors; and supplying or drawing current to the motor-generator based on said signals. In some embodiments, the method further comprises: retrieving a torque profile; adjusting the torque profile based on one or more of said parameters; outputting a torque control signal based on said adjusting; and supplying the current to the motor-generator based on said torque control signal. In some embodiments, the method further comprises: rectifying the current that is drawn from the motor-generator using a bridge circuit as a rectifier; and supplying current to the motor-generator using the bridge circuit as an inverter.

BRIEF DESCRIPTION OF DRAWINGS

The following drawings illustrate embodiments of the invention, which should not be construed as restricting the scope of the invention in any way.

DESCRIPTION

A. Glossary

The term "body segment" may refer to a part of a body, such as a thigh, for example. It may also refer to one or more muscles of the body segment, such as a hamstring and a quadriceps. Further, a body segment may also comprise multiple, constituent body segments, depending on how they are defined. Most muscle groups span across two joints. For instance, the hamstring (i.e. the biceps femoris and semitendinosus) spans from pelvis to tibia, and the quadriceps (including, e.g., the vastus intermedius) spans from upper femur to tibia via the patella and some tendons. As a consequence, contraction of a muscle may affect multiple skeletal body segments.

The term "electromyography" or EMG refers to the measurement of electrical muscle activity, which may be used to estimate joint torque more accurately than using more direct motion sensors.

The term "firmware" includes, but is not limited to, program code and data used to control and manage the interactions between the various modules of the system.

The term "hardware" includes, but is not limited to, the physical housing for a computer as well as the display if any, connectors, wiring, circuit boards having processor and memory units, power supply, and other electrical or electronic components.

The term "host" or "user" refers to a person or animal that is wearing an intermittent, body-segment motion-assisting system.

The term "module" can refer to any component in this invention and to any or all of the features of the invention without limitation. A module may be a software, firmware, hardware or mechanical module.

The term "motor-generator" when used herein refers to an electrical motor that is used as both a motor, i.e. for converting electrical energy to mechanical energy, and as a generator, for converting mechanical energy to electrical energy.

The term "negative power mode" or "negative mechanical power mode" refers to the muscle(s) of a body segment joint operating so as to oppose the direction the body segment is moving in. If the joint is extending then the muscle activity is applying a force to oppose that extension. If the joint is flexing, then the muscle activity is applying a force to oppose that flexion. This is analogous to viewing the product of angular velocity and torque about that joint being negative.

The term "positive power mode" or "positive mechanical power mode" refers to the muscle(s) of a body segment joint operating so as to support the direction the body segment is moving in. If the joint is extending then the muscle activity is applying a force to help that extension. If the joint is flexing, then the muscle activity is applying a force to help that flexion. This is analogous to viewing the product of angular velocity and torque about that joint being positive.

The term "processor" is used to refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). The processor performs the steps in the flowchart, whether they are explicitly described as being executed by the processor or whether the execution thereby is implicit due to the steps being described as performed by code or a module. The processor, if comprised of multiple processors, may be located together or separately from each other.

The term "software" includes, but is not limited to, program code that performs the computations necessary for calculating estimations, adjusting torque profiles, displaying information, and/or managing input and output data.

The term "system" when used herein without qualification refers to a system for intermittently assisting motion of a body segment, the system being the subject of the present invention. The system may embody further features, such as harvesting energy from the same or other body segments.

B. Overview

Figure 2:
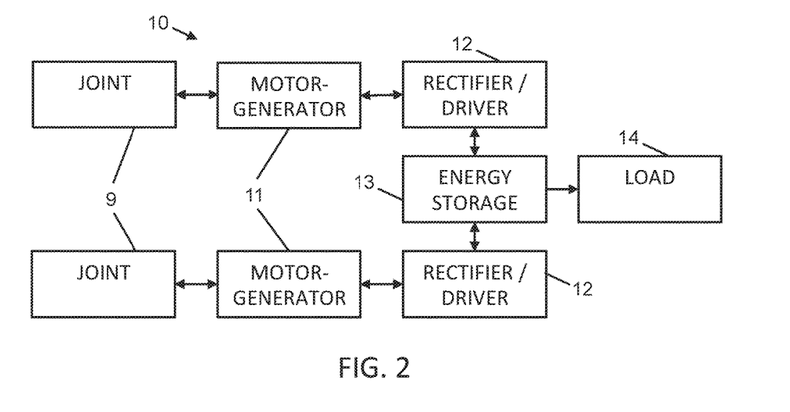
FIG. 2 is a simplified schematic block diagram of a system for intermittently assisting body segment movement, in accordance with some implementations of the present invention.

Referring to FIG. 2, two (for example) body joints 9 are shown connected to an intermittent body-segment motion assisting system 10. The joints 9 may be human knee joints, for example. In other embodiments, other human joints and/or animal joints may be used. Each joint 9 is connected to a motor-generator 11. Motor-generator 11 switches from being an electrical generator when it is operating in an energy-harvesting mode, to an electrical motor when it is operating to assist motion of a body-segment about a joint 9. Each motor-generator 11 is connected to a rectifier/driver circuit 12. When motor-generator 11 is operating in an energy-harvesting mode, i.e. as a generator, circuit 12 acts as a rectifier to rectify AC (alternating current) generated by the energy-harvesting generator into DC (direct current). In contrast, when motor-generator 11 is operating as a motor to assist with motion of the joint 9, it is controlled by circuit 12, which acts as a driver circuit. The same components (motor-generator 11 and rectifier/driver 12) are therefore used for both the energy harvesting and the motion-assistive modes, but in different ways. Circuits 12 are connected to an electrical energy storage unit 13 (such as a battery), which stores electrical energy harvested from motion of the joints 9 when the system 10 is operating as an energy harvester. Circuits 12 may include smoothing circuitry to reduce the voltage ripple of the rectified current. When the system 10 is providing energy to one or both of the joints 9, electrical energy is drawn from the energy storage unit 13.

As a result, the system 10 allows bi-directional energy flow between a joint 9 and energy storage unit 13. As such, mechanical energy from the body is converted to electrical energy, and then later converted back from electrical energy to mechanical energy for return to the body. Energy from the energy storage unit 13 may also be used to power other loads 14, such as a cellphone, laptop or radio battery charger. The load 14 may be connected directly to the rectifier/driver 12. It may be the case that one of the joints 9 is subjected to energy harvesting while at the same time the other joint is being assisted. In some embodiments, the system 10 may be attached to only one joint 9, in which case only one motor-generator and one rectifier/driver will be required.

C. Exemplary Embodiment

Figure 3:
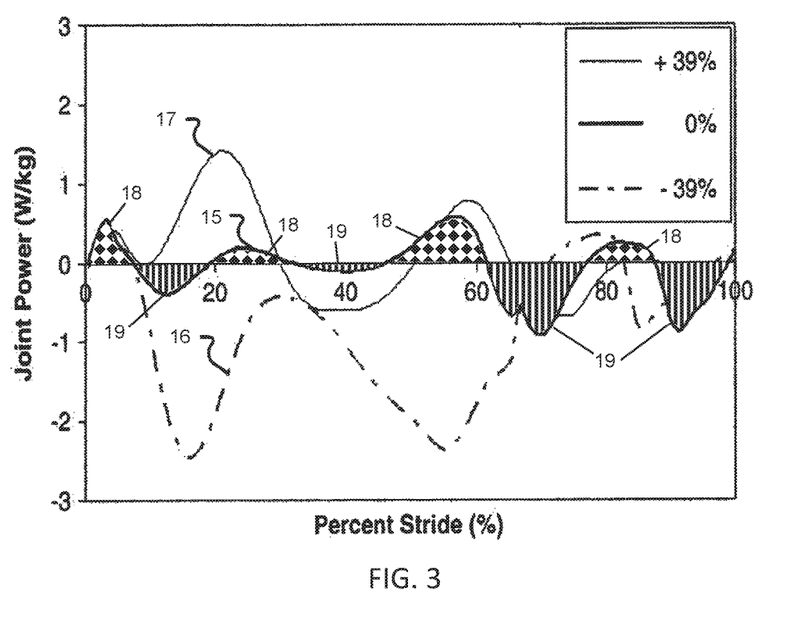
FIG. 3 is a graph showing negative and positive power modes for a knee joint during a walking gait cycle, on the flat and on ascending and descending grades.

Referring to FIG. 3, a plot 15 is shown of knee joint power for walking on level terrain, i.e. a 0° slope, for a complete cycle of knee joint motion, i.e. from 0-100%. Also shown is a plot 16 for knee joint power for walking down a slope of 39° and a plot 17 for knee joint power when walking up a 39° slope. Regions of positive power 18 are shown for plot 15 for walking on the level terrain. Regions of negative power 19 are also shown for plot 15 for walking on level terrain. System 10 is configured to assist motion of the knee joint when the knee is working in positive work modes. It can be seen from FIG. 3 that there are four parts 18 of a complete knee joint motion cycle in which the work mode of the knee is positive, when walking on the flat. The system 10 will therefore supply energy intermittently to the joint over a complete cycle of motion, i.e. at times corresponding to portions 18 of the cycle. It can also be seen from the plots that the timing and extent of the positive and negative work regions changes as the slope of the grade changes, and some regions completely disappear at extreme slopes. Note that there are other gait parameters that contribute to these changes. The system 10 will automatically adjust the timing of its assistance to the joint by estimating the type of gait. While still at the laboratory stage, it is envisioned that the use of contactless electromyography may alternately be used to measure the gait.

Figure 4:
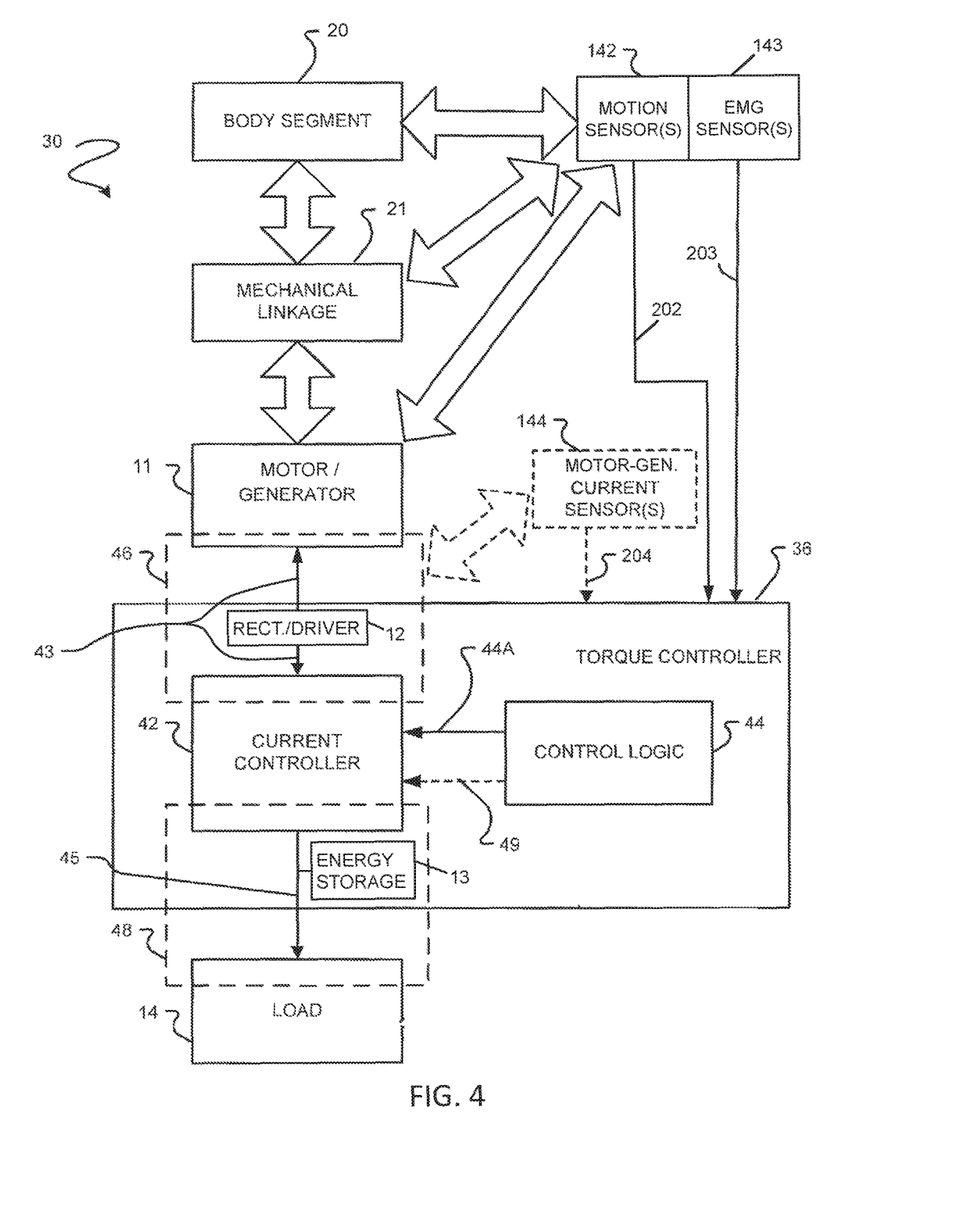
FIG. 4 is a schematic diagram of a body-segment assisting and biomechanical energy harvesting system, according to an example embodiment of the present invention.

FIG. 4 is a more detailed example of a system 30 for intermittently assisting motion of a body segment 20. A motor-generator 11 is coupled by mechanical linkage 21 to a body segment 20. The motor-generator 11 is electrically connected to a torque controller 36, which controls the motor torque developed by motor-generator when operating as a motor in an assistive mode. The torque controller may also control the torque of the motor-generator 11 when it is operating in energy harvesting mode, thereby controlling the amount of current channelled to the energy storage 13. Torque controller 36 may include energy storage 13, or energy storage 13 may be external to the torque controller. Torque controller 36 is electrically connected to an electrical load 14, and is configured to supply current from motor-generator 11 to load 14. In particular embodiments, torque controller 36 comprises a current controller 42, which controls the current supplied to the motor-generator 11 and (since this current is at least approximately proportional to the motor torque) thereby controls the motor torque developed by the motor-generator 11. In addition to (or as a part of) controlling the motor current/torque developed by motor-generator 11, torque controller 36 may perform the function of switching the electrical connection to the load 14 on and off and also controlling the amount of current supplied to the load.

Torque controller 36 comprises a current controller 42 and control logic 44. A motor-generator circuit 46 provides an electrical connection between motor-generator 11 and current controller 42. Motor-generator circuit 46 comprises an input/output 43 between the motor-generator 11 and the current controller 42. Connection 43 may operate as an output from the current controller 42 and an input to the motor-generator 11 when the system 30 is operating in assistive mode. Conversely, connection 43 may operate as an output from the motor-generator 11 and an input to the current controller 42 when the system 30 is operating in energy harvesting mode. A rectifier/driver circuit 12 is included in the motor-generator circuit 46. Generator circuit 46 may also comprise other circuit components not expressly shown, e.g. rectifying components, amplifiers, signal conditioning circuits, drivers, inverters, timers and/or the like.

A load circuit 48 provides the electrical connection between current controller 42 and load 14. Load circuit comprises an output 45 from current controller 42, which is electrically connected to load 14. The load circuit 48 also includes one or more energy storage units 13, for storing electrical energy harvested from the body segment 20 and for supplying energy to the motor-generator 11 when it is being used for assisting with motion of the body segment. Load circuit 48 may also comprise other circuit components not expressly shown, e.g. rectifying circuits, amplifiers, signal conditioning circuits, capacitors, super capacitors, rechargeable batteries and/or the like. Depending on the embodiment, load circuit 48 may be completely outside of the torque controller 36.

In the illustrated embodiment, torque controller 36 is configured to control the motor torque developed by motor-generator 11 by controlling the current supplied to the motor-generator. In particular, current controller 42 controls the current supplied to motor-generator 11 from motor-generator circuit 46. The current supplied to motor-generator 11 from motor-generator circuit 46 may be referred to herein as "motor current". Where motor-generator 11 is a permanent magnet synchronous machine (PMSM), the motor current is proportional, at least in a first order approximation, to the motor torque developed by motor-generator 11 when operating in assistive mode, and to the corresponding torques/forces applied to body segment 20. Accordingly, when more motor current is supplied to motor-generator 11, the motor torque is higher and the host (to which body segment 20 belongs) may be more significantly assisted by the activity of intermittent body-segment motion-assisting system 30. Conversely, when less motor current is supplied to motor-generator 11, the motor torque is lower and the host will be less assisted by the activity of intermittent body-segment motion-assisting system 30. It will also be appreciated that the amount of motor current supplied, and eventually converted to work applied to body segment 20 via mechanical linkage 21, impacts the amount of energy stored in energy storage 13. In some embodiments, an effort is made to balance the competing objectives of providing maximum amounts of assistance while minimizing the impact on the stored amount of energy, taking into consideration that during other parts of the motion of the body segment, energy harvesting may be occurring. Note that the relationship between the motor current and the motor torque is a roughly linear relationship for PMSMs (either DC or AC), but for AC induction motors (ACIM) it is not the case as there is a dependency on angular velocity as well. PMSMs are preferred because ACIMs are impractical for the power levels involved.

The torque controller may control the current supplied to the motor-generator continuously. This means that, during a period 18 in which the joint power is positive, the value of the current supplied to the motor-generator may be steady, may increase, may decrease, may both increase and decrease, or may follow a prescribed, more complex profile.

Still referring to FIG. 4, torque controller 36 receives input signal(s) 202 from one or more motion sensors 142 and/or input signal(s) 203 from one or more EMG sensor(s) 143 configured to detect various aspects of the motion of body segment 20, mechanical linkage 21 and/or motor-generator 11. By way of non-limiting example, motion sensors 142 may comprise encoders, accelerometers, gyroscopes, one or more varieties of position sensors and/or the like. In particular embodiments, motion sensors 142 and/or EMG sensor(s) 143 may detect one or more aspects of the motion of body segment 20 and provide motion sensor signals 202 which are indicative of the velocity of a point on a body segment 20, and/or the angular velocity of a body segment about a joint. In one particular embodiment, where body segment 20 comprises a knee joint, motion sensors 142 may provide a motion sensor signal 202 indicative of angular velocity about the knee joint. In other embodiments, motion sensors 142 may indicate some other aspect of motion of body segment 20. EMG sensors 143 measure electrical muscle activity of the body segment and may be used to estimate joint torque more accurately than a purely motion-based system. By way of a non-limiting example, motion sensors 142 may comprise one or more accelerometers configured to detect heel strike—i.e. the moment during gait when the host's heel strikes the ground.

In particular embodiments, motion sensors 142 comprise one or more sensors for detecting a frequency of a voltage output signal from motor-generator 11 which may be correlated with one or more aspects (e.g. the velocity) of the motion of body segment 20. For example, as discussed above, motor-generator 11 may output three phase electrical power and corresponding voltage signals. Motion sensor(s) 142 may detect a frequency of the voltage signal associated with one or more of these phases. This frequency may be correlated with (e.g. proportional to) the velocity of motion of body segment 20. In one particular embodiment, the three phase voltage signals output by motor-generator 11 are rectified, and filtered to remove ripple yielding a voltage output corresponding to the envelope of the angular velocity of motor-generator 11. This envelope is divided in two to provide an envelope midpoint. One or more of the three phase voltage signals output by motor-generator 11 may then be compared with the envelope midpoint to produce one or more corresponding digital signals whenever one of the phase voltage signals crosses the envelope midpoint. The edge-to-edge time of one or more of these digital signals may be measured to give the magnitude of their respective periods and inverted to get the frequency of motor-generator 11. The frequency of motor-generator 11 is directly proportional to the angular velocity of motor-generator and similarly correlated with (e.g. proportional to) the angular velocity about the knee joint (e.g. of body segment 20). It will be appreciated that any one of the phase voltage signals output from motor-generator 11 could be used to determine the magnitude of the angular velocity of body segment 20 or that a suitable combination (e.g. an average) of the angular velocities estimated from each phase voltage signal could be used. The direction of the angular velocity of body segment 20 may be given by examining the sequence of the three digital signals corresponding to the three phase voltage signals output from motor-generator 11.

Sensor signals 202 output from motion sensor(s) 142 may be conditioned by suitable signal conditioning circuitry (not shown) before or after being provided to torque controller 36.

Torque controller 36 may optionally receive a feedback signal 204 reflective of generator current drawn from motor-generator 11, or of drive current supplied to the motor-generator. In some embodiments, motor-generator current feedback signal 204 may be provided by one or more current sensor(s) 144. In other embodiments, motor-generator circuit 46 may be designed to provide motor-generator current feedback signal 204 directly, i.e. without the need for separate current sensor(s) 144. In some embodiments, current sensor(s) 144 may detect, and/or motor-generator current feedback signal 204 may be reflective of, the current drawn from motor-generator 11 after rectification—i.e. generator current feedback signal 204 may be reflective of a DC generator current level.

In the illustrated embodiment, current controller 42 controls the motor-generator current based at least in part on a torque control signal 44A (which may also be referred to as a torque reference signal 44A). For example, current controller 42 may attempt to cause the motor current of the motor-generator 11 to track torque control signal 44A. In the illustrated embodiment, torque control signal 44A is generated by control logic 44 and may be indicative of a magnitude of the desired motor torque to be developed in motor-generator 11 and/or a magnitude of the desired motor current to be supplied to motor-generator 11. Control logic 44 may comprise one or more suitably configured central processing units (CPU), one or more microprocessors, one or more microcontrollers, one or more field-programmable gate arrays (FPGA), application-specific integrated circuits (ASIC), logic circuits, combinations thereof or any other suitable processing unit(s) comprising hardware and/or firmware and/or software capable of functioning as described herein. In some embodiments, control logic 44 may be implemented in the analog domain by a suitably designed analog control circuit.

Current controller 42 may also optionally control the motor current (or the corresponding motor torque which may be at least approximately proportional to the motor current) based on optional voltage control signal 49. For example, current controller 42 may attempt to cause the motor current to track voltage control signal 49, or current controller 42 may limit the output current of motor-generator circuit 46 to a level indicated by voltage control signal 49.

In some embodiments, current controller 42 is configured to control the motor current supplied to motor-generator 11 and the corresponding motor torque by pulsing the power from motor-generator circuit 46 to motor-generator 11. For example, current controller 42 may be configured to repeatedly electrically connect and disconnect generator circuit 46 and motor-generator 11, and vary the motor current continuously such as by using duty cycle control or pulse-width modulated control, wholly within a period of time during which the operating mode of the body segment 20 is positive.

In some embodiments, current controller 42 is configured to control the amount of motor current/torque based on a motor-generator current feedback signal 204 which may be provided by one or more current sensors 144 and/or which may be obtained directly from motor-generator circuit 46. Motor-generator current feedback signal 204 may be indicative of an instantaneous motor-generator current/torque or of a time average motor-generator current/torque. By way of a non-limiting example, current controller 42 may be configured to control the motor-generator current/torque based on a difference between a motor-generator current feedback signal 204 and torque control signal 44A from control logic 44.

In some embodiments, current controller 42 may control the motor-generator current/torque based on a moving-window time average of the motor-generator current feedback signal 204. In some embodiments, motor-generator current feedback signal 204 may be time averaged in some manner prior to being provided to torque controller 36. In other embodiments, motor-generator current feedback signal 204 may be provided to control logic 44, which may generate torque control signal 44A based at least in part on motor-generator current feedback signal 204. In such embodiments, current controller 42 may not determine a difference between motor-generator current feedback signal 204 and torque control signal 44A.

In some embodiments, the system 30 may operate for a period in an energy-harvesting mode only to determine which portions of the gait correspond to positive work modes and which correspond to negative modes. After this determination, the system 30 may switch to working in a combined energy harvesting and body-segment assisting mode, or even to just a body-segment assisting mode.

Figure 5:
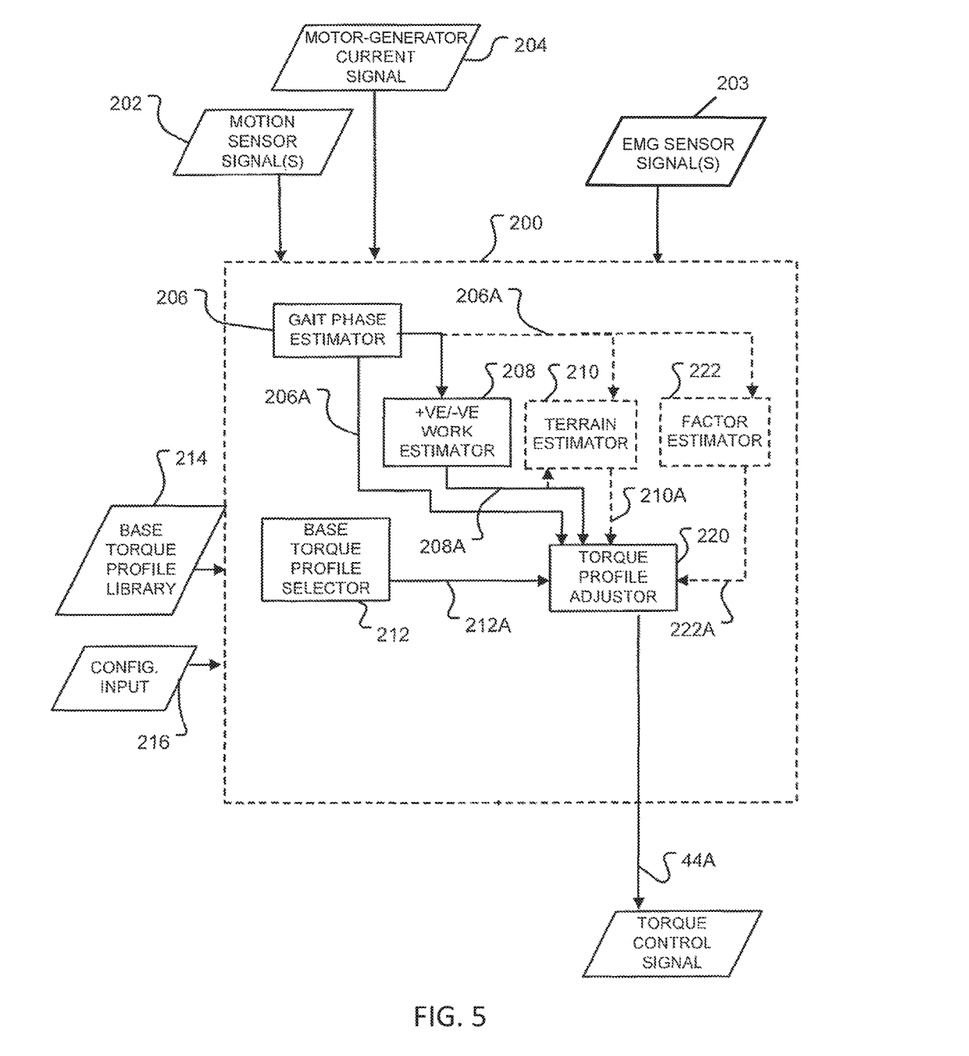
FIG. 5 schematically depicts control logic according to a particular embodiment of the invention, which may be used as part of the body-segment assisting and energy harvesting system of FIG. 4.

Referring to FIG. 5, control logic 200 is shown according to a particular embodiment. Control logic 200 may be used as, or as a part of, control logic 44 of body-segment assisting system 30 (FIG. 4) and may be used to determine torque control signal 44A discussed above. As mentioned briefly above and discussed in more detail below, in some embodiments, control logic 200 may also be used to determine optional voltage control signal 49. In the illustrated embodiment, control logic 200 receives a number of inputs, which include: motion sensor signal(s) 202 (e.g. from motion sensor(s) 142) indicative of one or more aspects of the motion of body segment 20; EMG sensor signal(s) 203 (e.g. from EMG sensor(s) 143) indicative of one or more aspects of the muscle activity of body segment 20; motor-generator current signal 204 (e.g. from motor-generator current sensor(s) 144) indicative of the current output of or current input to motor-generator 11; a base torque profile library input 214; and a configuration input 216. It will be appreciated that some of these inputs are optional—i.e. in some embodiments, all of these inputs are not necessary and control logic 200 may be able to perform some or all of its functions with a subset of these inputs. Further, it will be appreciated that in other embodiments, control logic 200 may be provided with one or more additional inputs that may be used to perform particular functions.

In the illustrated embodiment, control logic 200 is associated with body-segment assisting system 30 wherein body segment 20 is connected to a knee joint and where energy is supplied intermittently to the body segment when walking or running, for example.

In the illustrated embodiment, where body segment 20 comprises a knee joint and energy is applied thereto, control logic 200 comprises a gait phase estimator 206. Gait phase estimator 206 generates a gait phase estimate signal 206A indicative of the current phase of the gait of body segment 20 (e.g. the x-axis location in the exemplary level-terrain gait cycle of plot 15 in FIG. 3). Gait phase estimator 206 may use information from motion sensor signal(s) 202 and/or EMG sensor signals 203 to generate its gait phase estimate signal 206A. As discussed above, in some embodiments, motion sensor signal(s) 202 may comprise the three phase voltage output signals from motor-generator 11 which may be used to estimate the angular velocity of the motor-generator and the corresponding angular velocity of body segment 20. Gait phase estimator 206 may use this angular velocity information to generate gait phase estimate signal 206A. In some embodiments, gait phase estimator 206 may also make use of other inputs (e.g. motor-generator current feedback signal 204 or other inputs from other sensors) to generate its gait phase estimate signal 206A.

In some embodiments, it is not necessary to precisely estimate the gait phase—i.e. it is not necessary to precisely estimate the x-axis location in the FIG. 3 exemplary gait cycle plot 15. In some embodiments, gait phase estimator 206 may additionally or alternatively estimate whether the current gait phase is within one of the particular portions of a gait cycle which spans a range of gait phases—e.g. whether the knee joint is in swing flexion, swing extension, stance/collision flexion or stance extension. In one particular embodiment, gait phase estimator 206 may determine the transitions between gait phase portions and output information in gait phase estimate signal 206A indicating that a transition has occurred between gait portions.

Estimation of gait, phase of gait, change of phase of gait, and grade of terrain traversed are necessary only for model-based control, where the system is programmed with a model of what gait looks like. Such estimations are unnecessary for absolute control, where the torque created by the muscle is measured directly, such as by EMG muscle activity sensing.

In some embodiments, control logic 200 may operate in the form of a finite state machine that has states, each of which corresponds to a portion of repetitive motion of body segment 20 (e.g. portions of gait cycle 1).

There are many suitable techniques for estimating gait phase that may be used by gait phase estimator 206. Such techniques use a wide variety of motion sensors and corresponding motion sensor signals to estimate gait phase. Any such techniques could be used by gait phase estimator 206 in particular embodiments. Suitable exemplary and non-limiting techniques for gait phase estimation are described in:

WO2007/016781 by Donelan, J. M., Kuo, A. D., Hoffer, J. A., Li, Qingguo & Weber, D.;

Walking speed estimation using a shank-mounted inertial measurement unit, Li, Q., Young, M., Naing, V. & Donelan, J. M., Journal of Biomechanics, 43(8), 1640-1643, (2010);

Gait event detection using linear accelerometers or angular velocity transducers in able-bodied and spinal-cord injured individuals, Jasiewicz, J. M., Allum, J. H., Middleton, J. W., Barriskill, A., Condie, P., Purcell, B. & Li, R. C., Gait Posture 24 (4), 502-509, (2006); and Assessment of walking features from foot inertial sensing, Sabatini, A. M., Martelloni, C., Scapellato, S. & Cavallo, F., IEEE Transactions on Biomedical Engineering 52 (3), 486-494 (2005); all of which are hereby incorporated herein by reference.

It will be appreciated that gait phase estimator 206 is specific to situations where repetitive motion of body segment 20 is associated with gait. In other embodiments, where the repetitive motion of body segment 20 is different, gait phase estimator 206 may be replaced by a different phase estimator block, which may be used to estimate the phase of the different repetitive motion. In some embodiments, such phase estimator blocks may be particular to the particular type of repetitive motion of body segment 20.

Control logic 200 also comprises a positive/negative work estimator 208, which attempts to determine whether the motion of body segment 20 is in a positive or negative mechanical power mode. The output of the positive/negative work estimator 208 may be provided as output signal 208A which may be indicative of whether body segment 20 is operating in a positive or negative mechanical power mode. Positive/negative work estimator 208 may make use of a variety of information to ascertain whether the motion of body segment 20 is in a positive or negative mechanical power mode. By way of non-limiting example, such information may include gait phase estimate signal 206A, motion sensor signal(s) 202, EMG sensor signals 203, and/or motor-generator current feedback signal 204. In one particular non-limiting example, positive/negative work estimator 208 may use gait phase estimator signal 206A to determine the time of transitions between portions of a host's gait cycle and then estimate that a positive power region 8A (FIG. 3) would start after a transition from swing extension 6B to stance/collision flexion 7A. The duration of the positive power region 8A may be estimated by positive/negative work estimator 208 based a historical period of the stance/collision flexion portion of the host's gait, which may also be determined from gait phase estimate signal 206A. Similar methodology may be used to estimate the other positive mechanical power regions within a full cycle of the host's gait. Suitable exemplary techniques for estimating whether motion of body segment 20 is in a positive or negative mechanical power mode are described in WO2007/016781.

Control logic 200 may also comprise an optional terrain estimator 210 which may be used in embodiments where body segment 20 includes a portion of the host's body associated with locomotion (e.g. the host's knee or ankle joint). Terrain estimator may attempt to ascertain whether the motion of body segment 20 is being influenced by the terrain being traversed by the host. The output of terrain estimator 210 may be provided as output signal 210A, which may include, for example, an indication of the angular grade of the terrain being traversed by the host. Terrain estimator 210 may make use of a variety of information to generate terrain estimate signal 210A. By way of a non-limiting example, such information may include gait phase estimate signal 206A, positive/negative power mode signal 208A, motion sensor signal(s) 202, EMG sensor signals 203 and/or motor-generator current feedback signal 204 which may be analyzed over a past number of gait cycles, for example. Detecting terrain and slope types may be desirable to optimize body-segment motion assistance and/or energy harvesting during specific phases or portions of the gait, or to increase host comfort during more intense locomotion over difficult terrain.

Terrain represents just one of many types of factors which may have an impact on repetitive motion associated with body segment 20, the desirability of providing assistive power to the body segment at any given time and how much energy should be provided to the body segment at any given time. Such other types of factors may be estimated by optional factor estimator 222 to provide factor estimator output signal 222A. Factor estimator 222 may make use of a variety of information to generate factor estimator output signal 222A. By way of a non-limiting example, such information may include gait phase estimate signal 206A, positive/negative power mode signal 208A, terrain estimation signal 210A, motion sensor signal(s) 202 and/or motor-generator current feedback signal 204 and/or one or more other appropriate signals (e.g. sensor signals, user-configurable input information, calibration information and/or the like). Examples of factors which may be estimated by factor estimator 222 include, without limitation:

gait cadence which may influence the period of the repetitive motion in the time domain;

speed of movement of the host over ground;

host-specific gait parameters, which may influence the relative lengths of certain portions of repetitive motion (e.g. certain hosts of the same size walking on the same terrain at the same speed may have swing extension portions of different lengths relative to the lengths of other gait portions);

host size, which may influence the amplitudes of torques;

load carried by the host, which may influence the amplitude of torques;

location of carried load which may have different impact on different portions of the gait cycle (e.g. loads carried on the back might impact the stance portions relatively more heavily while loads carried on the legs might impact swing portions relatively more heavily); and/or locomotion type (e.g. walking, running, jogging, skipping, moving backwards, jumping and/or the like).

Some or all of the factors which may be estimated by factor estimator 222 may additionally or alternatively be specified as part of configuration input data 216 discussed further below.

Control logic 200 may comprise a base torque profile selector 212 which serves the purpose of selecting a base torque profile 212A from a library 214 of base torque profiles. Base torque profile library 214 may be stored in memory (not expressly shown) which may be a part of, or otherwise accessible to, control logic 200. Base torque profile library 214 may comprise a library of base torque profiles for many types of repetitive motions of many types of body segments 20. For example, base torque profile library 214 may comprise a number of base torque profiles for different types of repetitive motion (e.g. walking, running, jogging, skipping, moving backwards, jumping and/or the like) when body segment 20 comprises a knee joint and other types of base torque profiles for other types of repetitive motion and other types of body segments.

The selection of a particular base torque profile 212A by base torque profile selector 212 may be based, in part, on configuration input 216. By way of a non-limiting example, configuration input 216 may comprise user-configurable input information about the use of body-segment motion assistance system 30, experimentally determined information about the use of body-segment motion assistance system, calibration information about the use of body-segment motion assistance system, system constant information and/or the like. For example, a host may specify (as part of configuration input 216) that they are using body-segment motion assistance system 30 for walking and that the host wants to first harvest energy primarily during mutualistic conditions and then assist the body segments during their positive power modes after half an hour of walking.

Control logic 200 may comprise a torque profile adjuster 220 which adjusts the base torque profile (in an initial iteration) and/or a current torque profile (in subsequent iterations) in response to a variety of input information to provide (as output) torque control signal 44A. Torque control signal 44A may be provided to current controller 42 as discussed above. Torque profile adjuster 220 may receive input information which may include, without limitation: base torque profile 212A, gait phase estimator output 206A, positive/negative work estimator output 208A, terrain estimator output 210A, factor estimator output 222A, configuration input 216, motion sensor signal(s) 202 and/or motor-generator current signal 204. While not explicitly shown in the schematic illustration of FIG. 5, torque profile adjustor 220 may maintain a current torque profile which includes the most recent updates to the torque profile to be tracked. The current torque profile may be saved in accessible memory or the like and may provide the basis for torque control signal 44A output from torque profile adjuster 220.

Non-limiting examples of types of adjustments that may be made to torque profiles by torque profile adjustor 220 include, without limitation:

scaling and/or offsetting the entire torque profile in the torque domain (e.g. to compensate for host size);

scaling and/or offsetting of the entire torque profile in the time domain or in a "percentage of gait cycle" domain (e.g. to compensate for gait cadence);

scaling and/or offsetting of portions of the torque profile (e.g. one or more portions of the torque profile, one or more sub-parts of a portion in a torque profile and/or one or more transition periods between portions in a torque profile) in the torque domain (e.g. to more efficiently provide assistive power to a body segment throughout a gait cycle);

scaling and/or offsetting of portions of the torque profile (e.g. one or more portions of the torque profile, one or more sub-parts of a portion in a torque profile and/or one or more transition periods between portions in a torque profile) in the time domain or in a "percentage of gait cycle" domain (e.g. to compensate for different host gait profiles or to ensure host safety);

scaling and/or offsetting of the rate(s) of transitions (e.g. torque profile slopes) between different torque levels in a torque profile;

offsetting the location(s) in the time domain or in a "percentage of gait cycle" domain of changes in a torque profile; and/or scaling of the entire torque profile to a constant level.

Figure 6:
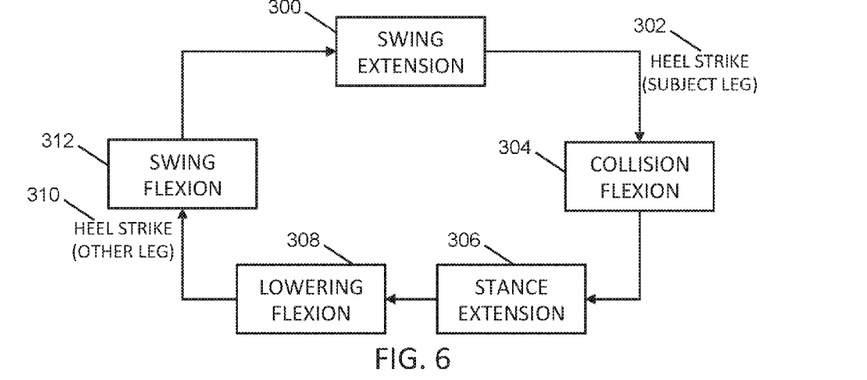
FIG. 6 is a state diagram of various states of a knee joint.

Simplified states that the control logic 200 may use when operating at least in part as a finite state machine are shown in FIG. 6. The states of a complete gait cycle are shown, starting from swing extension 300, during which the subject leg is swinging from a bent position behind the body to a straight position in front of the body. At the end of the swing extension state 300, i.e. when the heel strikes the ground 302, the collision flexion state 304 starts. In the collision flexion state the leg bends slightly at the knee, with the foot on the ground, during which the body's weight is transferred to the subject leg. This is followed by the stance extension state 306, in which the subject leg straightens out while the foot is still on the ground, propelling the body forward. The following state is the lowering flexion state 308, in which the subject leg that is supporting the body's weight bends slightly in order for the other leg to reach forwards more before its heel strikes the ground 310. After the heel of the other leg has struck the ground 310, the swing flexion state 312 commences, in which the subject leg is lifted from the ground behind the body, continuing the bending motion that started during the lowering flexion state 308. After the subject leg has finished bending in state 312, the swing extension state 300 starts again. Each state may be a positive or negative power phase, or include both a negative and positive power phase, and the torque applied in each state may either be positive or negative or both, depending on the assistance provided and/or whether energy is harvested. As can be appreciated, a more complex finite state machine, with more narrowly defined states, may be used.

Figure 7:
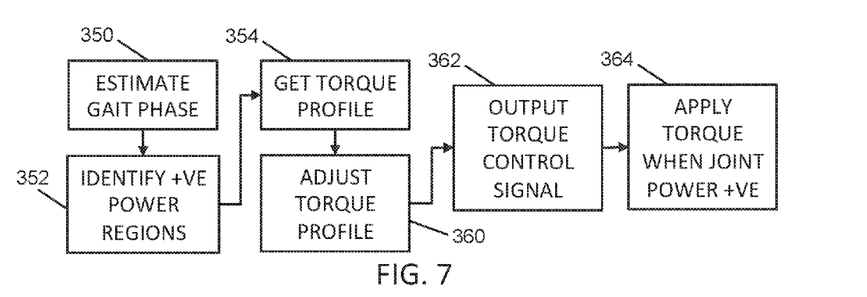
FIG. 7 is a flowchart of a process carried out by the body-segment motion assisting system, according to an embodiment of the present invention.

A flow chart is shown in FIG. 7 of the main steps the system 30 takes. In step 350, the system 30 estimates the phase of the host's gait, using, for example, the gait phase estimator 206. In step 352, the system 30 identifies positive power regions of the gait. In step 354, the system retrieves an appropriate torque profile for the identified gait and positive power regions. The torque profile that has been obtained may optionally be adjusted in step 360, which may be done by the system 30 acting automatically, or under a command from the host. In step 362, the system 30 outputs a torque control signal for controlling the current supplied to the motor-generator 11. Based on the torque control signal, the system 30 then, in step 364, applies torque to the body segment when it is operating in a positive power mode.

Figure 8:
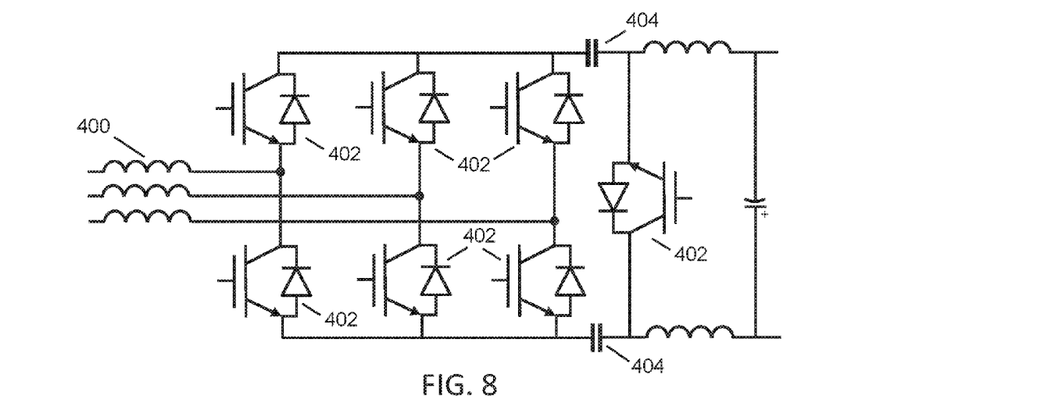
FIG. 8 is a basic schematic diagram of a 3-phase bridge that may be used as either a rectifier or an inverter.

Referring to FIG. 8, an exemplary circuit diagram of a 3-phase bridge is shown that can be used as rectifier/driver circuit 12 (FIG. 2). The inductances 400 represent the windings of the motor-generator 11. The 3-phase bridge includes actively controlled switches 402 and can be used either as a 3-phase synchronous rectifier for rectifying current produced by the motor-generator 11, or as a switch-mode power supply (switch-mode converter) for supplying current to the motor-generator. The motor-generator windings 400 are used as an inductor component for the switch-mode power supply. As is known, there are different variations of the 3-phase bridge that could be used as alternatives to the non-limiting example of FIG. 8. For example, the series capacitors 404 may be eliminated in some embodiments. There are other topologies to efficiently implement a bi-directional 3-phase converter, including shunt resistors from output of each phase to ground, and/or including some with two switches per phase.

D. Variations

In general, unless otherwise indicated, singular elements may be in the plural and vice versa with no loss of generality.

Throughout the description, specific details have been set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The detailed description has been presented partly in terms of methods or processes, symbolic representations of operations, functionalities and features of the invention. These method descriptions and representations are the means used by those skilled in the art to most effectively convey the substance of their work to others skilled in the art. A software implemented method or process is here, and generally, understood to be a self-consistent sequence of steps leading to a desired result. These steps require physical manipulations of physical quantities. Often, but not necessarily, these quantities take the form of electrical or magnetic signals or values capable of being stored, transferred, combined, compared, and otherwise manipulated. It will be further appreciated that the line between hardware and software is not always sharp, it being understood by those skilled in the art that the software implemented processes described herein may be embodied in hardware, firmware, software, or any combination thereof. Such processes may be controlled by coded instructions such as microcode and/or by stored programming instructions in one or more tangible or non-transient media readable by a computer or processor. The code modules may be stored in any computer storage system or device, such as hard disk drives, optical drives, solid state memories, etc. The methods may alternatively be embodied partly or wholly in specialized computer hardware, such as ASIC or FPGA circuitry.

Although the present invention has been illustrated principally in relation to a human knee joint, it has application in respect of other human joints and also animal joints.

The present invention may be used in an intermittent body-segment assistive mode only, with energy being drawn only from a pre-charged battery and not from a harvesting mode. In other embodiments, the battery may be pre-charged and the system 30 may be used in both harvesting and assistive modes.

While the Exemplary Embodiment is of the best presently contemplated mode of carrying out the subject matter disclosed and claimed herein, it will be clear to one having skill in the art that variations to the specific details disclosed herein can be made, resulting in other embodiments that are within the scope of the invention disclosed. Steps in the flowchart may be performed in a different order, other steps may be added, or one or more may be removed without altering the main function of the system. Modules of the system may be divided into constituent module or they may be duplicated. The division of functions between the various blocks of circuitry may be changed without altering the overall functions of the system. All parameters and configurations described herein are examples only and actual values of such depend on the specific embodiment. Accordingly, the scope of the invention is to be construed in accordance with the substance defined by the following claims.

The invention claimed is:

1. A system for intermittently assisting movement of a body segment of a user comprising:
  a motor-generator;
  a mechanical linkage configured to transmit mechanical power from the motor-generator to the body segment;
  a circuit configured to supply current to the motor-generator when the body segment is moving in a positive power mode, said circuit configured to prevent supply of current to the motor-generator when the body segment is moving in a negative power mode; and
  a bridge in the circuit that functions both as:
    a rectifier when current is drawn from the motor-generator; and
    an inverter when current is supplied to the motor-generator.

2. The system of claim 1, wherein the bridge is a 3-phase bridge.

3. The system of claim 1, wherein:
the movement of the body segment is repeated over a plurality of cycles; and
the circuit is configured to supply current to the motor-generator multiple times within each cycle.

4. The system of claim 1, wherein the circuit is configured to draw current from the motor-generator when the body segment is moving in a negative power mode.

5. The system of claim 4, further comprising an energy storage unit which stores electrical energy generated by the motor-generator when current is drawn from the motor-generator.

6. The system of claim 5, wherein the current that is supplied to the motor-generator is discharged from the energy storage unit.

7. The system of claim 6, wherein:
the movement of the body segment is repeated over a plurality of cycles; and
the circuit supplies current to and draws current from the motor-generator multiple times within each cycle.

8. The system of claim 6, wherein the circuit continually controls an amount of the current which is supplied to the motor-generator when the body segment is moving in the positive power mode.

9. The system of claim 4, further comprising one or more sensors configured to detect one or more parameters of movement of the body segment, said circuit configured to receive signals from said sensors and supply current to or draw current from the motor-generator based on said signals.

10. The system of claim 4, further comprising one or more sensors configured to detect one or more parameters of muscle activity of the body segment, said circuit configured to receive signals from said sensors and supply current to or draw current from the motor-generator based on said signals.

11. The system of claim 9, wherein the body segment is connected to a knee joint and said parameters include one or more of position, angular position, velocity, angular velocity, gait, phase of gait, change of phase of gait, and grade of terrain traversed as a result of said movement.

12. The system of claim 11, wherein said circuit comprises logic for estimating when the body segment is moving in a positive power mode and when the body segment is moving in a negative power mode.

13. A method for intermittently assisting movement of a body segment of a user comprising:
mechanically linking a motor-generator to the body segment such that mechanical power produced by the motor-generator assists movement of the body segment;
identifying positive power modes of said movement;
supplying current to the motor-generator when the body segment is moving in a positive power mode;
preventing supply of current to the motor-generator when the body segment is moving in other than a positive power mode;
rectifying the current that is drawn from the motor-generator using a bridge circuit as a rectifier; and
supplying current to the motor-generator using the bridge circuit as an inverter.

14. The method of claim 13, wherein the movement of the body segment is repeated over a plurality of cycles, the method further comprising:
supplying the current to the motor-generator multiple times within each cycle; and
drawing current from the motor-generator when the body segment is moving in a negative power mode.

15. The method of claim 14, further comprising continually controlling an amount of the current which is supplied to the motor-generator when the body segment is moving in the positive power mode.

16. The method of claim 14, further comprising:
sensing one or more parameters of movement or muscle activity of the body segment;
receiving signals from said sensors; and
supplying current to or drawing current from the motor-generator based on said signals.

17. The method of claim 14, wherein the body segment is connected to a knee joint and said parameters include one or more of position, angular position, velocity, angular velocity, gait, phase of gait, change of phase of gait, and grade of terrain traversed as a result of said movement.

18. The method of claim 14, further comprising:
retrieving a torque profile;
adjusting the torque profile based on one or more of said parameters;
outputting a torque control signal based on said adjusting; and
supplying the current to the motor-generator based on said torque control signal.

* * * * *